US008003652B2

(12) United States Patent
Koverech et al.

(10) Patent No.: US 8,003,652 B2
(45) Date of Patent: *Aug. 23, 2011

(54) USE OF ACETYL L-CARNITINE IN COMBINATION WITH PROPIONYL L-CARNITINE AND SILDENAFIL FOR THE TREATMENT OF ERECTILE DYSFUNCTION

(75) Inventors: Aleardo Koverech, Rome (IT); Giorgio Cavallini, Ferrara (IT)

(73) Assignee: Sigma-Tau Industrie Farmaceutiche Riunite, S.p.A., Rome (IT)

( * ) Notice: Subject to any disclaimer, the term of this patent is extended or adjusted under 35 U.S.C. 154(b) by 609 days.

This patent is subject to a terminal disclaimer.

(21) Appl. No.: 11/719,011

(22) PCT Filed: Oct. 19, 2005

(86) PCT No.: PCT/EP2005/011238
§ 371 (c)(1),
(2), (4) Date: May 10, 2007

(87) PCT Pub. No.: WO2006/050794
PCT Pub. Date: May 18, 2006

(65) Prior Publication Data
US 2008/0090906 A1    Apr. 17, 2008

(30) Foreign Application Priority Data
Nov. 11, 2004  (IT) .............................. RM2004A0561

(51) Int. Cl.
*A61K 31/497*    (2006.01)
*A61K 31/19*    (2006.01)

(52) U.S. Cl. .................................. 514/252.18; 514/554
(58) Field of Classification Search ............ 514/252.18, 514/554
See application file for complete search history.

(56) References Cited

FOREIGN PATENT DOCUMENTS

| WO | WO 01126666 | | 4/2001 |
|---|---|---|---|
| WO | WO-03/032751 | * | 4/2003 |
| WO | WO03/047563 | * | 6/2003 |
| WO | WO 2004/054567 | | 11/2003 |
| WO | WO 03/047563 | | 6/2006 |

OTHER PUBLICATIONS

Zippe et al., Urology, 2000;55:241-245.*
G. Cavallini, et al., Carnitine Versus Androgen Administration in Treatment . . . , Adult Urology, vol. 63, No. 4, pp. 641-646, XP002361866, 2004.
G. Cavallini, et al., Acetyl-L-Carnitine Plus Propionyl-L-Carnitine Improve Efficacy . . . , Adult Urology, vol. 66, No. 5, pp. 1080-1085, XP005158378, 2005.

* cited by examiner

*Primary Examiner* — San-Ming Hui
(74) *Attorney, Agent, or Firm* — Lucas & Mercanti, LLP

(57) ABSTRACT

The use of acetyl L-carnitine in combination with propionyl L-carnitine and sildenafil is described for the preparation of a medicament and/or dietetic product for the treatment of erectile dysfunction secondary to all those conditions in which there is distress or iatrogenic damage of the lesser pelvis within which the neurovascular bundles of the penis run.

4 Claims, No Drawings

USE OF ACETYL L-CARNITINE IN COMBINATION WITH PROPIONYL L-CARNITINE AND SILDENAFIL FOR THE TREATMENT OF ERECTILE DYSFUNCTION

The present invention relates to the use of acetyl L-carnitine and sildenafil for the preparation of a medicament for the treatment of erectile dysfunction (ED) secondary to all those conditions in which there is distress or iatrogenic damage or trauma of the lesser pelvis within which the neurovascular bundles of the penis run.

Damage to the lesser pelvis within which the neurovascular bundles of the penis run can be caused, for example, by radical retropubic prostatectomy (rrp) without bilateral sparing of the neurovascular bundles, by bilateral nerve-sparing radical retropubic prostatectomy (bnsrrp); by prostate irradiation for cancer; or by rectal surgery.

The percentage of patients with erectile dysfunction secondary to radical retropubic prostatectomy for cancer is approximately 100% in the absence of bilateral nerve sparing, and approximately 50% after bnsrrp.

The erectile deficit secondary to bnsrrp is due to transection of the accessory pudendal arteries which act as the main cavernous arteries or is due to incomplete safeguarding of the nerves.

Early intracavernous injection of alprostadil significantly, enhances the restoration of erectile function after bnsrrp. The use of selective 5-phosphodiesterase inhibitors has recently been introduced for the therapy of erectile dysfunction secondary to rrp or bnsrrp.

Vardenafil, tadalafil and sildenafil (Urology 2000; 55: 241-245) permit recovery of sexual function in approximately 15% of patients undergoing rrp, or in approximately 45% of patients undergoing bnsrrp.

In the medical field the use of acetyl L-carnitine and propionyl L-carnitine is already known.

WO03047563 describes the use of propionyl L-carnitine, alone or in combination with sildenafil, for the treatment of erectile dysfunction.

EP0539336 describes the use of L-carnitine and a number of alkanoyl L-carnitines for the treatment of idiopathic oligoasthenospermia.

U.S. Pat. No. 5,863,940 describes the use of L-carnitine in combination with acetyl L-carnitine for the treatment of idiopathic oligoasthenospermia.

WO03084526 describes the combined use of L-carnitine, acetyl L-carnitine and propionyl L-carnitine for the treatment of oligoasthenospermia.

U.S. Pat. No. 6,653,349 describes the use of acetyl L-carnitine in combination with propionyl L-carnitine for the treatment of renal dysfunctions.

Numerous other patents and publications describe the use of acetyl L-carnitine and propionyl L-carnitine for therapeutic and/or nutritional purposes, but none of the documents cited above describe these compounds as agents useful for enhancing the efficacy, for example, of sildenafil in the treatment of erectile dysfunction secondary to all those conditions in which there is distress or iatrogenic damage of the lesser pelvis within which the neurovascular bundles of the penis run.

Other compounds useful for the treatment of erectile dysfunction are also known.

For example, in *Int. Urol. Nephrol* 2001; 32 (3), 403-7 the use of sildenafil for the treatment of erectile dysfunction is described.

In *Salute Europa* dated Jun. 11, 2001 are presented the first data, published in the *British Journal of Urology*, regarding the experimentation in Italia and Europe with sublingual apomorphine for the treatment of erectile dysfunction.

Numerous other publications describe the use of compounds useful for the treatment of erectile dysfunction, none of which describe the use of acetyl L-carnitine and propionyl L-carnitine as agents useful for enhancing the efficacy of sildenafil in the treatment of erectile dysfunction according to the present invention.

The drugs known to be useful for the treatment of E.D. are not free of drawbacks.

For example, in *Eur. Urol.* 2001 August; 40 (2): 176-80 it is reported that not all patients respond to treatment with sildenafil.

In *Salute Europa* dated Jun. 11, 2001 it is reported that not all patients respond to treatment with apomorphine.

In *Hosp. Med.* 1998 October; 59 (10): 777 and in *Br. J. Urol.* 1996 October; 78(4): 628-31 it is reported that the administration of prostaglandin E1 and papaverine, respectively, is performed via the intracavernous route, and the discomfort caused by such administration is well known.

There is therefore a strongly perceived need for the availability of new drugs for the treatment of erectile dysfunction which do not present the drawbacks of the known drugs mentioned above.

It has now been found that the use of acetyl L-carnitine in combination with propionyl L-carnitine, or one of their pharmaceutically acceptable salts, enhances the efficacy of drugs known to be useful for the treatment of erectile dysfunction secondary to all those conditions in which there is distress or iatrogenic damage of the lesser pelvis within which the neurovascular bundles of the penis run.

What is meant by pharmaceutically acceptable salt of acetyl L-carnitine and propionyl L-carnitine is any salt prepared by addition of an acid to the acetyl L-carnitine or propionyl L-carnitine inner salt, and which does not give rise to unwanted toxic or side effects. The formation of salts by addition of acids is a well known practice in pharmaceutical technology.

Non-limitative examples of these salts are: chloride, bromide, orotate, aspartate, acid aspartate, citrate, acid citrate, magnesium citrate, phosphate, acid phosphate, fumarate, acid fumarate, magnesium fumarate, glycerophosphate, lactate, maleate and acid maleate, mucate, oxalate, acid oxalate, pamoate, acid pamoate, sulphate, acid sulphate, glucose phosphate, tartrate, acid tartrate, magnesium tartrate, 2-amino ethanesulphonate, magnesium 2-amino ethanesulphonate, methane-sulphonate, choline tartrate, trichloroacetate, and trifluoroacetate.

One subject of the present invention is therefore the combination of acetyl L-carnitine, propionyl L-carnitine, or one of their pharmaceutically acceptable salts, with one or more drugs useful for the treatment of erectile dysfunction. Non-limitative examples of said drugs useful for the treatment of erectile dysfunction are: sildenafil, vardenafil, tadalafil apomorphine, prostaglandin E1, phentolamine, and papaverine, in their various pharmaceutical preparations.

A further subject of the present invention consists in pharmaceutical and/or dietetic compositions containing as their active ingredient acetyl L-carnitine, propionyl L-carnitine, or one of their pharmaceutically acceptable salts, in combination with one or more of said drugs useful for the treatment of erectile dysfunction, and at least one pharmaceutically acceptable excipient and/or diluent.

A further subject of the present invention is the use of acetyl L-carnitine and propionyl L-carnitine, or one of their pharmaceutically acceptable salts, for the preparation of a medicament and/or dietetic product for the treatment of erectile dysfunction.

A further subject of the present invention is the use of acetyl L-carnitine and propionyl L-carnitine, or one of their pharmaceutically acceptable salts, in combination with one of more of said useful drugs, for the preparation of a medicament and/or dietetic product for the treatment of erectile dysfunction.

A further subject of the present invention is the use of acetyl L-carnitine and propionyl L-carnitine, alone or in combination with one or more of said useful drugs, for the preparation of a medicament and/or dietetic product for the treatment of erectile dysfunction secondary to all those conditions in which there is distress, iatrogenic damage or trauma of the lesser pelvis within which the neurovascular bundles of the penis run, in which said damage is caused, for example, by radical retropubic prostatectomy without bilateral saving of the neurovascular bundles; by bilateral nerve-saving radical retropubic prostatectomy; by prostate irradiation for cancer; or by rectal surgery.

The following examples illustrate the invention.

EXAMPLE 1

To assess the activity of the combination according to the invention for the treatment of erectile dysfunction, a randomised, double-blind placebo-controlled clinical trial was conducted.

The patients entered into the trial had to meet the following inclusion criteria:
erectile dysfunction secondary to radical retropubic prostatectomy, with or without bilateral sparing of the neurovascular bundles, in patients in whom the prostatectomy had been performed at least 6 months but less than 2 years prior to entry into the clinical trial;
complete erectile function prior to the prostatectomy (this information had to be confirmed by the partner or documented in the patient's hospital file;
not on medical treatment for prostate cancer;
not on treatment for erectile dysfunction before or after prostatectomy;
normal total and free prostate antigen values;
involvement in a heterosexual relationship for at least 6 months prior to surgery.

Patients presenting the following characteristics were not included in the trial:
hormone imbalance;
patients taking drugs interacting significantly with the study compounds;
cerebral or cardiac ischaemia episodes during the past 6 months;
excessive alcohol or cigarette consumption;
chronic liver disease;
abnormal liver function (aspartate and alanine transaminase alterations);
diabetes;
decompensated hypertension and hypotension;
prostate cancer.

The patients recruited into the study were divided into two main groups on the basis of whether or not they had undergone bilateral nerve sparing surgery (rrp and bnsrrp).

These two groups were further subdivided into the following subsets:
a) placebo;
b) sildenafil 100 mg;
c) sildenafil 100 mg+propionyl L-carnitine 2 g+acetyl L-carnitine 2 g;
d) propionyl L-carnitine 2 g;
e) acetyl L-carnitine 2 g.
f) propionyl L-carnitine 2 g+acetyl L-carnitine 2 g;
g) sildenafil 100 mg+propionyl L-carnitine 2 g;
h) sildenafil 100 mg+acetyl L-carnitine 2 g.

The carnitines (acetyl L-carnitine and propionyl L-carnitine) were administered orally twice daily (1 g×2/day).

Sildenafil was administered (as required) and taken 1-2 hours before sexual intercourse at a dose of 100 mg.

The placebo was administered in the place of acetyl L-carnitine and/or propionyl L-carnitine and/or sildenafil.

After 4 months' treatment the following variables were analysed:

1. erectile function (evaluated by "IIEF-15" scores: IIEF=International Index of Erectile Function);

2. satisfaction with sexual intercourse (IIEF-15);

3. orgasm (IIEF-15);

4. general sexual well-being (IIEF-15);

5. recording of nocturnal penile tumescence (NPT) [evaluated with RigiScan (Dacomed-Minnesota). A >70% increase in rigidity compared to baseline at the base of the penis and >60% at the upper end of the penis, a >2 cm increase in circumference at the upper end of the penis and >3 cm at the base were considered "complete erection". The total duration (minutes) of the recording period on three nights was assessed.

The results obtained, evaluated statistically using the ANOVA test, are given in the tables here below.

TABLE 1

Patients undergoing bilateral nerve-sparing radical retropubic prostatectomy (bnsrrp).
Erectile function
IIEF 15 Score

| | | mean ± s.d. | p < (vs sildenafil after therapy) |
|---|---|---|---|
| Placebo | Before therapy | 11.3 ± 3.6 | — |
| | After therapy | 11.7 ± 3.7 | — |
| Sildenafil 100 mg | Before therapy | 11.9 ± 4.0 | — |
| | After therapy | 21.7 ± 6.8 | — |
| Sildenafil 100 mg + propionyl L-carnitine 2 g + acetyl L-carnitine 2 g | Before therapy | 12.5 ± 5.4 | — |
| | After therapy | 27.3 ± 4.6 | 0.05 |
| Propionyl L-carnitine 2 g | Before therapy | 12.2 ± 3.9 | — |
| | After therapy | 18.1 ± 3.2 | NS |
| Acetyl L-carnitine 2 g | Before therapy | 11.3 ± 3.8 | — |
| | After therapy | 17.2 ± 3.5 | NS |
| Propionyl L-carnitine 2 g + acetyl L-carnitine 2 g | Before therapy | 11.6 ± 3.2 | — |
| | After therapy | 24.3 ± 2.6 | NS |
| Sildenafil 100 mg + propionyl L-carnitine 2 g | Before therapy | 11.7 ± 3.3 | — |
| | After therapy | 24.1 ± 2.0 | NS |
| Sildenafil 100 mg + acetyl L-carnitine 2 g | Before therapy | 11.9 ± 3.6 | — |
| | After therapy | 23.0 ± 2.0 | NS |

TABLE 2

Patients undergoing bilateral nerve-sparing
radical retropubic prostatectomy (bnsrrp)
Satisfaction with sexual intercourse
IIEF 15 score

|  |  | mean ± s.d. | p < (vs sildenafil after therapy) |
|---|---|---|---|
| Placebo | Before therapy | 3.2 ± 1.1 | — |
|  | After therapy | 3.1 ± 0.6 | — |
| Sildenafil 100 mg | Before therapy | 3.1 ± 1.1 | — |
|  | After therapy | 4.8 ± 2.5 | — |
| Sildenafil 100 mg + propionyl L-carnitine 2 g + acetyl L-carnitine 2 g | Before therapy | 3.0 ± 1.4 | — |
|  | After therapy | 8.9 ± 4.7 | 0.01 |
| Propionyl L-carnitine 2 g | Before therapy | 3.2 ± 1.2 | — |
|  | After therapy | 3.9 ± 1.1 | NS |
| Acetyl L-carnitine 2 g | Before therapy | 3.1 ± 1.1 | — |
|  | After therapy | 4.0 ± 1.1 | NS |
| Propionyl L-carnitine 2 g + acetyl L-carnitine 2 g | Before therapy | 3.2 ± 1.3 | — |
|  | After therapy | 6.1 ± 2.1 | NS |
| Sildenafil 100 mg + propionyl L-carnitine 2 g | Before therapy | 3.2 ± 1.3 | — |
|  | After therapy | 6.3 ± 1.6 | NS |
| Sildenafil 100 mg + acetyl L-carnitine 2 g | Before therapy | 3.2 ± 1.3 | — |
|  | After therapy | 6.2 ± 1.1 | NS |

TABLE 3

Patients undergoing bilateral nerve-sparing
radical retropubic prostatectomy (bnsrrp)
Orgasm
IIEF 15 score

|  |  | mean ± s.d. | p < (vs sildenafil after therapy) |
|---|---|---|---|
| Placebo | Before therapy | 3.1 ± 0.8 | — |
|  | After therapy | 3.0 ± 0.6 | — |
| Sildenafil 100 mg | Before therapy | 3.0 ± 0.9 | — |
|  | After therapy | 5.9 ± 2.9 | — |
| Sildenafil 100 mg + propionyl L-carnitine 2 g + acetyl L-carnitine 2 g | Before therapy | 3.0 ± 1.0 | — |
|  | After therapy | 8.8 ± 2.6 | 0.01 |
| Propionyl L-carnitine 2 g | Before therapy | 3.0 ± 1.1 | — |
|  | After therapy | 4.1 ± 1.1 | NS |
| Acetyl L-carnitine 2 g | Before therapy | 3.2 ± 1.1 | — |
|  | After therapy | 4.0 ± 0.9 | NS |
| Propionyl L-carnitine 2 g + acetyl L-carnitine 2 g | Before therapy | 2.9 ± 0.9 | — |
|  | After therapy | 6.5 ± 1.1 | NS |
| Sildenafil 100 mg + propionyl L-carnitine 2 g | Before therapy | 3.1 ± 1.0 | — |
|  | After therapy | 6.4 ± 1.1 | NS |
| Sildenafil 100 mg + acetyl L-carnitine 2 g | Before therapy | 3.0 ± 1.1 | — |
|  | After therapy | 6.3 ± 1.2 | NS |

TABLE 4

Patients undergoing bilateral nerve-sparing
radical retropubic prostatectomy (bnsrrp)
General sexual well-being
IIEF 15 score

|  |  | mean ± s.d. | p < (vs sildenafil after therapy) |
|---|---|---|---|
| Placebo | Before therapy | 3.3 ± 0.9 | — |
|  | After therapy | 2.8 ± 0.7 | — |
| Sildenafil 100 mg | Before therapy | 2.7 ± 1.0 | — |
|  | After therapy | 5.4 ± 2.7 | — |
| Sildenafil 100 mg + propionyl L-carnitine 2 g + acetyl L-carnitine 2 g | Before therapy | 2.8 ± 0.7 | — |
|  | After therapy | 8.6 ± 2.0 | 0.01 |
| Propionyl L-carnitine 2 g | Before therapy | 2.9 ± 1.6 | — |
|  | After therapy | 4.1 ± 0.9 | NS |
| Acetyl L-carnitine 2 g | Before therapy | 2.9 ± 1.0 | — |
|  | After therapy | 3.9 ± 1.1 | NS |
| Propionyl L-carnitine 2 g + acetyl L-carnitine 2 g | Before therapy | 2.8 ± 1.1 | — |
|  | After therapy | 6.4 ± 1.2 | NS |
| Sildenafil 100 mg + propionyl L-carnitine 2 g | Before therapy | 2.8 ± 0.8 | — |
|  | After therapy | 3.9 ± 0.9 | NS |
| Sildenafil 100 mg + acetyl L-carnitine 2 g | Before therapy | 2.9 ± 1.2 | — |
|  | After therapy | 3.9 ± 0.8 | NS |

TABLE 5

Patients undergoing bilateral nerve-sparing
radical retropubic prostatectomy (bnsrrp)
Recording of nocturnal penile tumescence (NPT)
Minutes

|  |  | mean ± s.d. | p < (vs sildenafil after therapy) |
|---|---|---|---|
| Placebo | Before therapy | 74.3 ± 12.6 | — |
|  | After therapy | 69.6 ± 18.0 | — |
| Sildenafil 100 mg | Before therapy | 70.4 ± 13.2 | — |
|  | After therapy | 85.9 ± 14.3 | — |
| Sildenafil 100 mg + propionyl L-carnitine 2 g + acetyl L-carnitine 2 g | Before therapy | 69.5 ± 11.4 | — |
|  | After therapy | 110.3 ± 21.3 | 0.01 |
| Propionyl L-carnitine 2 g | Before therapy | 68.2 ± 13.5 | — |
|  | After therapy | 77.1 ± 16.1 | NS |
| Acetyl L-carnitine 2 g | Before therapy | 70.8 ± 14.9 | — |
|  | After therapy | 79.0 ± 12.3 | NS |
| Propionyl L-carnitine 2 g + acetyl L-carnitine 2 g | Before therapy | 66.5 ± 14.8 | — |
|  | After therapy | 101.1 ± 13.0 | 0.01 |
| Sildenafil 100 mg + propionyl L-carnitine 2 g | Before therapy | 72.5 ± 14.3 | — |
|  | After therapy | 93.1 ± 14.8 | NS |
| Sildenafil 100 mg + acetyl L-carnitine 2 g | Before therapy | 71.4 ± 12.7 | — |
|  | After therapy | 91.2 ± 12.7 | NS |

TABLE 6

Patients undergoing radical retropubic
prostatectomy (rrp) without bilateral sparing of
the neurovascular bundles.
Erectile function
IIEF 15 score

|  |  | mean ± s.d. | p < (vs sildenafil after therapy) |
|---|---|---|---|
| Placebo | Before therapy | 3.5 ± 1.3 | — |
|  | After therapy | 3.4 ± 2.6 | — |
| Sildenafil 100 mg | Before therapy | 3.8 ± 2.9 | — |
|  | After therapy | 9.2 ± 1.9 | — |
| Sildenafil 100 mg + propionyl L-carnitine 2 g + acetyl L-carnitine 2 g | Before therapy | 2.9 ± 1.0 | — |
|  | After therapy | 14.1 ± 4.9 | 0.01 |
| Propionyl L-carnitine 2 g | Before therapy | 3.3 ± 1.1 | — |
|  | After therapy | 4.0 ± 1.1 | NS |

TABLE 6-continued

Patients undergoing radical retropubic
prostatectomy (rrp) without bilateral sparing of
the neurovascular bundles.
Erectile function
IIEF 15 score

|  |  | mean ± s.d. | p < (vs sildenafil after therapy) |
|---|---|---|---|
| Acetyl L-carnitine 2 g | Before therapy | 3.2 ± 1.1 | — |
|  | After therapy | 4.1 ± 1.0 | NS |
| Propionyl L-carnitine 2 g + acetyl L-carnitine 2 g | Before therapy | 3.2 ± 1.0 | — |
|  | After therapy | 10.2 ± 1.1 | NS |
| Sildenafil 100 mg + propionyl L-carnitine 2 g | Before therapy | 3.4 ± 1.1 | — |
|  | After therapy | 10.1 ± 1.1 | NS |
| Sildenafil 100 mg + acetyl L-carnitine 2 g | Before therapy | 3.4 ± 1.2 | — |
|  | After therapy | 10.3 ± 1.1 | NS |

TABLE 7

Patients undergoing radical retropubic
prostatectomy (rrp) without bilateral sparing
of the neurovascular bundles.
Satisfaction with sexual intercourse
IIEF 15 score

|  |  | mean ± s.d. | p < (vs sildenafil after therapy) |
|---|---|---|---|
| Placebo | Before therapy | 2.0 ± 0.8 | — |
|  | After therapy | 1.6 ± 0.9 | — |
| Sildenafil 100 mg | Before therapy | 1.3 ± 0.8 | — |
|  | After therapy | 2.9 ± 1.6 | — |
| Sildenafil 100 mg + propionyl L-carnitine 2 g + acetyl L-carnitine 2 g | Before therapy | 1.5 ± 1.0 | — |
|  | After therapy | 3.5 ± 0.2 | 0.05 |
| Propionyl L-carnitine 2 g | Before therapy | 1.7 ± 0.4 | — |
|  | After therapy | 1.9 ± 0.6 | NS |
| Acetyl L-carnitine 2 g | Before therapy | 1.8 ± 0.8 | — |
|  | After therapy | 1.9 ± 0.6 | NS |
| Propionyl L-carnitine 2 g + acetyl L-carnitine 2 g | Before therapy | 1.8 ± 0.2 | — |
|  | After therapy | 1.9 ± 0.2 | NS |
| Sildenafil 100 mg + propionyl L-carnitine 2 g | Before therapy | 1.6 ± 0.7 | — |
|  | After therapy | 1.9 ± 0.7 | NS |
| Sildenafil 100 mg + acetyl L-carnitine 2 g | Before therapy | 1.8 ± 0.7 | — |
|  | After therapy | 1.9 ± 0.6 | NS |

TABLE 8

Patients undergoing radical retropubic
prostatectomy (rrp) without bilateral sparing
of the neurovascular bundles.
Orgasm
IIEF 15 score

|  |  | mean ± s.d. | p < (vs sildenafil after therapy) |
|---|---|---|---|
| Placebo | Before therapy | 0.8 ± 0.7 | — |
|  | After therapy | 0.8 ± 0.6 | — |
| Sildenafil 100 mg | Before therapy | 0.9 ± 0.6 | — |
|  | After therapy | 2.2 ± 0.9 | — |
| Sildenafil 100 mg + propionyl L-carnitine 2 g + acetyl L-carnitine 2 g | Before therapy | 0.8 ± 0.7 | — |
|  | After therapy | 3.2 ± 1.5 | 0.05 |
| Propionyl L-carnitine 2 g | Before therapy | 0.7 ± 0.3 | — |
|  | After therapy | 1.0 ± 0.3 | NS |
| Acetyl L-carnitine 2 g | Before therapy | 0.8 ± 0.6 | — |
|  | After therapy | 0.9 ± 0.4 | NS |

TABLE 8-continued

Patients undergoing radical retropubic
prostatectomy (rrp) without bilateral sparing
of the neurovascular bundles.
Orgasm
IIEF 15 score

|  |  | mean ± s.d. | p < (vs sildenafil after therapy) |
|---|---|---|---|
| Propionyl L-carnitine 2 g + acetyl L-carnitine 2 g | Before therapy | 0.6 ± 0.3 | — |
|  | After therapy | 1.7 ± 0.3 | NS |
| Sildenafil 100 mg + propionyl L-carnitine 2 g | Before therapy | 0.7 ± 0.4 | — |
|  | After therapy | 1.8 ± 0.6 | NS |
| Sildenafil 100 mg + acetyl L-carnitine 2 g | Before therapy | 0.9 ± 0.3 | — |
|  | After therapy | 1.6 ± 0.4 | NS |

TABLE 9

Patients undergoing radical retropubic
prostatectomy (rrp) without bilateral sparing
of the neurovascular bundles.
General sexual well-being
IIEF 15 score

|  |  | mean ± s.d. | p < (vs sildenafil after therapy) |
|---|---|---|---|
| Placebo | Before therapy | 1.2 ± 0.7 | — |
|  | After therapy | 0.9 ± 0.7 | — |
| Sildenafil 100 mg | Before therapy | 1.1 ± 0.8 | — |
|  | After therapy | 2.4 ± 2.0 | — |
| Sildenafil 100 mg + propionyl L-carnitine 2 g + acetyl L-carnitine 2 g | Before therapy | 1.0 ± 0.8 | — |
|  | After therapy | 4.0 ± 1.7 | 0.05 |
| Propionyl L-carnitine 2 g | Before therapy | 1.3 ± 0.5 | — |
|  | After therapy | 1.4 ± 0.5 | NS |
| Acetyl L-carnitine 2 g | Before therapy | 1.0 ± 0.4 | — |
|  | After therapy | 1.2 ± 0.5 | NS |
| Propionyl L-carnitine 2 g + acetyl L-carnitine 2 g | Before therapy | 1.2 ± 0.6 | — |
|  | After therapy | 1.2 ± 0.5 | NS |
| Sildenafil 100 mg + propionyl L-carnitine 2 g | Before therapy | 1.1 ± 0.2 | — |
|  | After therapy | 1.5 ± 0.3 | NS |
| Sildenafil 100 mg + acetyl L-carnitine 2 g | Before therapy | 1.3 ± 0.5 | — |
|  | After therapy | 1.2 ± 0.5 | NS |

TABLE 10

Patients undergoing radical retropubic
prostatectomy (rrp) without bilateral
sparing of the neurovascular bundles.
Recording of nocturnal penile tumescence (NPT)
Minutes

|  |  | mean ± s.d. | p < (vs sildenafil after therapy) |
|---|---|---|---|
| Placebo | Before therapy | 36.2 ± 10.3 | — |
|  | After therapy | 37.4 ± 10.4 | — |
| Sildenafil 100 mg | Before therapy | 37.1 ± 8.5 | — |
|  | After therapy | 39.1 ± 7.9 | — |
| Sildenafil 100 mg + propionyl L-carnitine 2 g + acetyl L-carnitine 2 g | Before therapy | 37.1 ± 9.6 | — |
|  | After therapy | 58.6 ± 14.6 | 0.001 |
| Propionyl L-carnitine 2 g | Before therapy | 35.0 ± 9.1 | — |
|  | After therapy | 36.4 ± 5.3 | NS |
| Acetyl L-carnitine 2 g | Before therapy | 37.7 ± 8.8 | — |
|  | After therapy | 38.2 ± 5.7 | NS |
| Propionyl L-carnitine 2 g + acetyl L-carnitine 2 g | Before therapy | 36.4 ± 8.3 | — |
|  | After therapy | 50.1 ± 7.1 | 0.001 |

TABLE 10-continued

Patients undergoing radical retropubic prostatectomy (rrp) without bilateral sparing of the neurovascular bundles. Recording of nocturnal penile tumescence (NPT) Minutes

| | | mean ± s.d. | p < (vs sildenafil after therapy) |
|---|---|---|---|
| Sildenafil 100 mg + propionyl L-carnitine 2 g | Before therapy After therapy | 34.3 ± 6.2 35.5 ± 74 | — NS |
| Sildenafil 100 mg + acetyl L-carnitine 2 g | Before therapy After therapy | 37.2 ± 6.8 35.5 ± 6.8 | — NS |

The results obtained and reported in Tables 1-10 show that there are no significant differences in baseline values in the various groups and that the administration of placebo did not significantly modify these values.

Treatment with the combination according to the invention invariably yielded statistically significantly superior results as compared to the group treated with sildenafil alone in the tests reported in Tables 1-10.

Significantly superior results were obtained in the group treated with the combination of acetyl L-carnitine and propionyl L-carnitine without sildenafil as compared to the group treated with sildenafil alone, in the tests recording nocturnal penile tumescence (Tables 5 and 10). In addition, in the course of the clinical trial a number of patients treated with the combination of acetyl L-carnitine and propionyl L-carnitine, without simultaneously taking sildenafil, reported experiencing improvements and satisfactory sexual intercourse.

Acetyl L-carnitine and propionyl L-carnitine administered singly or separately together with sildenafil never showed statistically significant superior activity compared to the group treated with sildenafil alone.

The combination according to the invention, in any form, may be suitable for administration to human subjects, the preferred administration route being oral administration.

Acetyl L-carnitine and propionyl L-carnitine and the drug useful for the treatment of erectile dysfunction can be formulated together, as a mixture, or can be formulated separately (packaged separately) using known methods.

On the basis of various factors, such as the concentration of active ingredients or the patient's condition, the combination according to the invention can be marketed as a food supplement, a nutritional supplement, or as a therapeutic product on sale with or without a compulsory doctor's prescription.

The combination according to the invention, when in unit dose form, contains from 50 mg to 4 g of acetyl L-carnitine inner salt, and from 4 g to 50 mg of propionyl L-carnitine inner salt, or an equimolar amount of one of their pharmaceutically acceptable salts, and a suitable dose of the drug useful for the treatment of erectile dysfunction.

The dose recommended, according to the present invention, is 2 g/day of acetyl L-carnitine and 2 g/day of propionyl L-carnitine, and 100 mg of sildenafil once or twice a week.

The daily dose will depend, according to the judgement of the primary care physician, on the patient's weight, age and condition. Larger doses of acetyl L-carnitine and propionyl L-carnitine can be administered thanks to the extremely low toxicity of said active ingredients.

The combination according to the present invention can be prepared by mixing the active ingredients with suitable excipients for the formulation of pharmaceutical and/or dietetic compositions which can be administered to human subjects or to animals.

Experts in pharmaceutical technology are familiar with said excipients.

The combination according to the present invention can also additionally contain one or more vitamins and/or natural lipophilic and/or hydrophilic antioxidants such as, for example, vitamin E, vitamin A, vitamin C, GSH or selenium.

Acetyl L-carnitine, propionyl L-carnitine and sildenafil are known compounds which can be procured at the chemist's shop or pharmacy.

The invention claimed is:

1. Method of treating erectile dysfunction in a patient who has undergone retropubic prostatectomy consisting of administering to a patient who has undergone retropubic prostatectomy a combination consisting of
   2 g of acetyl L-carnitine, 2 g of propionyl L-carnitine or a pharmaceutically acceptable salt thereof; and
   sildenafil, in their various pharmaceutical preparations.

2. The method of claim 1, in which the pharmaceutically acceptable salt is selected from the group consisting of chloride, bromide, orotate, aspartate, acid aspartate, citrate, acid citrate, magnesium citrate, phosphate, acid phosphate, fumarate, acid fumarate, magnesium fumarate, glycerophosphate, lactate, maleate and acid maleate, mucate, oxalate, acid oxalate, pamoate, acid pamoate, sulphate, acid sulphate, glucose phosphate, tartrate, acid tartrate, magnesium tartrate, 2-amino ethanesulphonate, magnesium 2-amino ethanesulphonate, methanesulphonate, choline tartrate, trichloroacetate and trifluoroacetate.

3. A composition consisting of
   a) 2 g of acetyl L-carnitine, 2 g of propionyl L-carnitine or pharmaceutically acceptable salts thereof;
   b) sildenafil; and
   c) at least one pharmaceutically acceptable excipient or diluent.

4. A composition consisting of
   a) 2 g of acetyl L-carnitine, 2 g of propionyl L-carnitine or pharmaceutically acceptable salts thereof;
   b) sildenafil; and
   c) at least one pharmaceutically acceptable excipient or diluent, one or more vitamins and lipophilic or hydrophilic antioxidants.

* * * * *